United States Patent [19]

Foley et al.

[11] 4,310,673
[45] Jan. 12, 1982

[54] XANTHENE COMPOUNDS

[75] Inventors: James W. Foley, Andover; Louis Locatell, Jr., Wellesley Hills; Charles M. Zepp, Boylston, all of Mass.

[73] Assignee: Polaroid Corporation, Cambridge, Mass.

[21] Appl. No.: 194,464

[22] Filed: Oct. 6, 1980

Related U.S. Application Data

[63] Continuation-in-part of Ser. No. 106,905, Dec. 26, 1979, Pat. No. 4,258,118.

[51] Int. Cl.³ .............................................. C07D 275/04
[52] U.S. Cl. ................................................... 548/207
[58] Field of Search ......................... 548/207; 430/221

[56] References Cited

U.S. PATENT DOCUMENTS

| | | | |
|---|---|---|---|
| 1,879,537 | 9/1932 | Schneider | 430/520 |
| 1,994,876 | 3/1935 | Schneider et al. | 430/520 |
| 2,182,794 | 12/1939 | Dawson | 430/517 |
| 2,203,767 | 6/1940 | Baldsiefen | 430/517 |
| 2,203,768 | 6/1940 | Baldsiefen | 430/517 |
| 2,350,090 | 5/1944 | Beilenson | 430/520 |
| 3,005,711 | 10/1961 | Burgardt et al. | 430/520 |
| 3,406,069 | 10/1968 | Overman | 430/520 |
| 3,615,548 | 10/1971 | Firestine | 430/520 |

OTHER PUBLICATIONS

*Bielstein's Handbuch der Organischen Chemie,* vol. 27, p. 534.

*Primary Examiner*—Nicholas S. Rizzo
*Attorney, Agent, or Firm*—Sybil A. Campbell

[57] ABSTRACT

The present invention is concerned with novel xanthene compounds of the formula

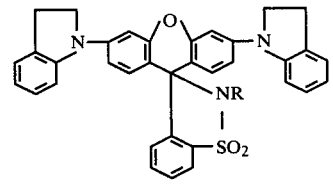

wherein R is hydrogen or alkyl, which compounds are useful in photographic products and processes.

3 Claims, No Drawings

XANTHENE COMPOUNDS

CROSS-REFERENCE TO RELATED APPLICATIONS

This application is a continuation-in-part of Ser. No. 106,905 filed Dec. 26, 1979, now U.S. Pat. No. 4,258,118.

BACKGROUND OF THE INVENTION

1. Field of the Invention

This invention relates to novel xanthene compounds and to their use, e.g., as light-screening dyes in photographic products and processes.

2. Description of the Prior Art

It is well known that photographic film, and especially multicolor films, may and generally do vary from lot to lot, notwithstanding efforts to "repeat" previous films. Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films are stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within vary narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer films, with the added complication that once the film is shipped, the sensitometric properties are essentially fixed. The opportunity for adjustment provided in darkroom processing, practically speaking, is unavailable for users of selfdeveloping films. While professional and advanced amateur photographers may be skillful enough to utilize color correction filters to at least partially "rebalance" the color balance, ordinary users of the film would only be confused by such additional operations.

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an antihalation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity, fog or exert other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color may reappear in time.

Among the classes of light-screening dyes used previously are the triarylmethanes and xanthenes. For example, U.S. Pat. Nos. 1,879,537; 1,994,876; 2,350,090 and 3,005,711 disclose the use of fuchsone-type dyes in antihalation layers, and U.S. Pat. Nos. 3,406,069 and 3,615,548 are concerned with the metal chelates of fuchsone dyes as antihalation dyes. These and other types of triarylmethane dyes suffer from one or more of the drawbacks discussed above, and in particular, prior dyes of this type have been difficult to keep decolorized at the pH's normally encountered during processing subsequent to "bleaching" and in the final product. Xanthenes have been employed in antihalation layers that are removed during photographic processing. For example, U.S. Pat. Nos. 2,182,794; 2,203,767 and 2,203,768 disclose the use of rhodamine dyes in certain antihalation layers that are removed during processing in an acid bath or a plain water rinse bath depending upon the solubility characteristics of the particular layer.

Aforementioned U.S. patent application Ser. No. 106,905 is directed to photographic products and processes employing light-screening dyes of the formula

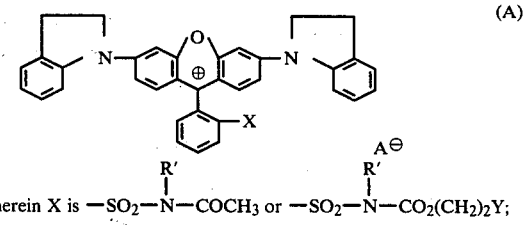

(A)

wherein X is $-SO_2-\overset{R'}{\underset{|}{N}}-COCH_3$ or $-SO_2-\overset{R'}{\underset{|}{N}}-CO_2(CH_2)_2Y$;

R' is alkyl; Y is an electron-withdrawing group and A is an anion. These compounds are colored, i.e., capable of absorbing visible radiation, and at an alkaline pH, are converted to a colorless product by undergoing an irreversible cleavage reaction with base. The colorless product formed is a new compound which is different from and non-reversible to the colored compound by a change in pH. In particular, it is the X group substituted on the phenyl moiety that undergoes the irreversible cleavage reaction in alkaline solution that is complete within a predetermined time at a predetermined alkaline pH to give the new colorless compound, namely, the cyclic sulfonamide,

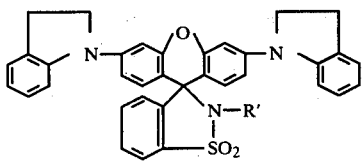
(B)

wherein R' has the same meaning given above. These compounds offer advantages over the light-screening dyes previously used because of their ability to decolorize completely and irreversibly to a substantially inert colorless product.

Besides being the product of the cleavage reaction, the compounds of formula B and also such compounds wherein the N atom of the cyclic sulfonamido ring is unsubstituted are useful as intermediates in the synthesis of the compounds of formula A. For example, as discussed in said application, the compounds of formula A may be prepared (a) by reacting sulfonefluorescein dichloride with indoline to give the di(indolinyl)-substituted compound of the formula

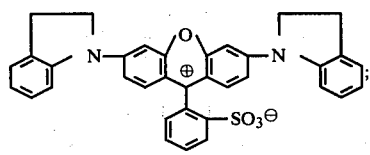

(b) reacting said di(indolinyl)-substituted compound with phosphorous pentachloride or thionyl chloride to give the corresponding sulfonyl chloride of the formula

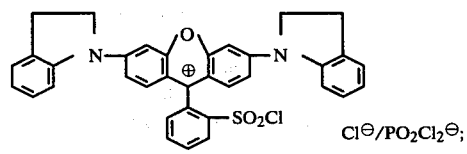

(c) reacting said sulfonyl chloride with ammonia to give the corresponding cyclic sulfonamide of the formula

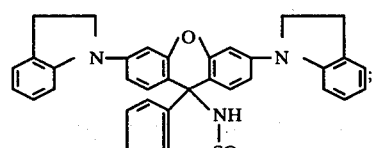

(d) reacting said cyclic sulfonamide with an alkylating agent to give the corresponding N-R' sulfonamide of the formula

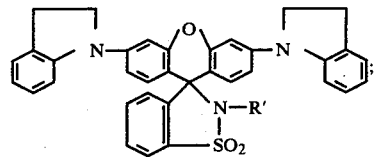

(e) reacting said N-R' sulfonamide with a reducing agent to give the corresponding reduction product of the formula

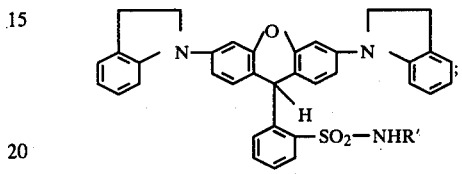

(f) reacting said reduction product with the appropriate acylating agent, for example, $ClCOCH_3$ or $ClCO_2(CH_2)_2Y$ to give the leuco dye precursor of the formula

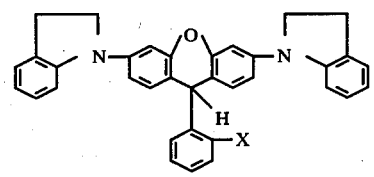

wherein X is $-SO_2-\overset{R'}{\underset{|}{N}}-COCH_3$ or $-SO_2-\overset{R'}{\underset{|}{N}}-CO_2(CH_2)_2Y$, R' is alkyl and Y is an electron-withdrawing group; and (g) oxidizing said leuco dye precursor preferably using o-chloranil as the oxidizing agent followed by isolating the dye product from its o-chloranil complex with an acid to yield the dye product. Optionally, the compound of step (a) also may be synthesized in a stepwise fashion by replacing only one of the chloro groups of the starting sulfonefluorescein dichloride with an indolinyl group and then reacting this intermediate with indoline to replace the remaining chloro group.

The present invention is directed to the xanthene compounds produced in steps (c) and (d) above. These compounds are not only useful as intermediates in the synthesis of certain light-screening dyes but also have been found useful as light-screening dyes per se.

SUMMARY OF THE INVENTION

It is therefore the primary object of the present invention to provide certain xanthene compounds.

It is another object of the present invention to provide xanthene compounds useful in photographic products and processes.

Other objects of this invention will in part be obvious and will in part appear hereinafter.

This invention accordingly comprises the products and compositions possessing the features, properties and the relation of elements which are exemplified in the following detailed disclosure and the scope of the application of which will be indicated in the claims.

For a fuller understanding of the nature and objects of the present invention, reference should be had to the following detailed description.

DETAILED DESCRIPTION OF THE INVENTION

The compounds provided by the present invention may be represented by the formula

wherein R is hydrogen or alkyl, usually lower alkyl having 1 to 4 carbon atoms, and preferably methyl.

The subject xanthene compounds, though also useful as photographic light-screening dyes, do not undergo an irreversible cleavage reaction but decolorize in response to a change in pH. These pH-sensitive dyes are initially colored, i.e., capable of absorbing visible radiation at a given pH, usually about pH 4 or below and are converted to a colorless or non-light-absorbing form above said pH. Because of their ability to decolorize completely in base without requiring an additional reagent, such as, a sulfite for the "bleaching" reaction and because they remain colorless in aqueous solution over a pH range of about 4.5 to 14, they may be retained in the photographic light-sensitive element without the possibility of color reappearing in time. Besides being non-staining, the compounds usually are substantially inert with respect to the light-sensitive material and thus, may be positioned, for example, in a layer adjacent to a silver halide emulsion layer without having any adverse effect on the properties of the emulsion.

As noted above, the subject compounds may be synthesized in the manner described in aforementioned application Ser. No. 106,905 by reacting sulfonefluorescein dichloride with indoline to give the di(indolinyl)-substituted compound which is reacted with phosphorus pentachloride or thionyl chloride to give the corresponding sulfonyl chloride followed by treating with ammonia to produce the cyclic sulfonamide. Where the R group is alkyl, the cyclic sulfonamide is reacted with the selected alkylating agent to give the corresponding N-alkylated sulfonamide.

The following examples are given to further illustrate the present invention and are not intended to limit the scope thereof.

EXAMPLE 1

Preparation of the compound having the formula

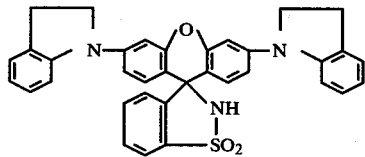

(a) A mixture of 81 g (0.2 M) of sulfonefluorescein dichloride (3,6-dichlorosulfofluorescein)

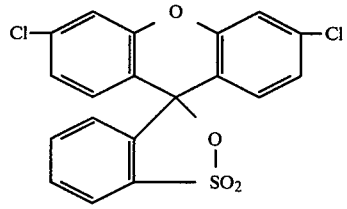

and 100 g (0.84 M) of indoline in 3300 ml absolute methanol was heated at reflux for three hours. After a short time, the product began to precipitate from solution. The product was filtered hot, washed with ethanol (2×500 ml), diethyl ether (2×500 ml), air dried overnight and then dried in vacuo to give 107.4 g of the compound

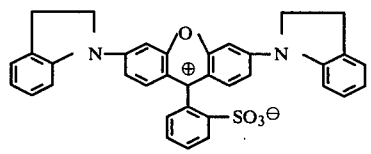

(b) The compound of step (a) 100 g (0.175 M) in 1500 ml of chloroform was treated with 73 g (0.35 M) of phosphorus pentachloride. The stirred mixture was heated at reflux for approximately 5 hours, then allowed to stir overnight while cooling to room temperature. The mixture was treated with 500 ml water (no exotherm was observed at this stage) and then allowed to stir for 10 minutes. The mixture was transferred to a 4000 ml separatory funnel and the chloroform layer separated. The chloroform layer was washed with water (2×1000 ml) and dried over anhydrous magnesium sulfate. The magnesium sulfate was filtered, and the filtrate containing the corresponding sulfonylchloride compound

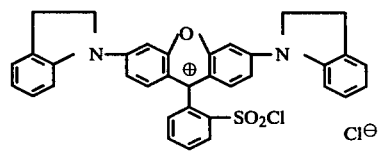

was cooled to 0° C. (dry ice-acetone bath).

(c) The filtrate of step (b) was then saturated with anhydrous ammonia. The mixture was filtered to remove the NH$_4$Cl and the solvent evaporated under reduced pressure. The residue was continuously extracted with methanol by the use of a Soxhlet extractor over the weekend. The light blue solid which remained was dried in vacuo to give 71.8 g of the title compound. This material was essentially single spot on TLC (chloroform) R$_f$=0.41; a minor component was observed at the origin (starting material). Melting range 258°–61° C. (d).

EXAMPLE 2

Preparation of the compound having the formula

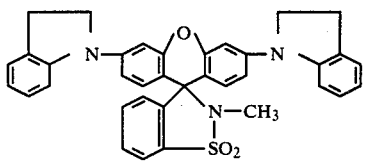

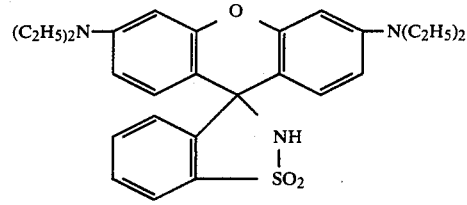

Compound X

The results are set forth in the Table below.

TABLE

| Compound | pH 4 | pH 5 | pH 6 | pH 7 |
| --- | --- | --- | --- | --- |
| Ex 1 | + | o | o | o |
| Ex 2 | + | o | o | o |
| Cpd X | +++ | +++ | ++ | + |

+++ = very intense color
++ = intense color
+ = faint color
o = no color

A slurry of the compound of Example 1 60 g (0.11 M) in 750 ml diglyme (previously dried over 4A molecular sieves) was treated with 14.8 g (0.132 M) of potassium t-butoxide and allowed to stir at room temperature for about 45 minutes during which time solution takes place. The dark-brown solution was cooled in an icebath and treated with 12.5 ml (16.65 g; 0.132 M) of dimethyl sulfate all at once. The resulting mixture was allowed to warm to room temperature with stirring overnight.

The mixture was worked up in two portions. Approximately one half of the reaction mixture was poured into 3500 ml water containing 175 g of sodium chloride with stirring. After stirring for about 15 minutes, the product was filtered, washed voluminously with water and dried in vacuo. The other half of the reaction mixture was worked up in the same manner to yield 59.6 g of the title compound. This material was essentially single spot by TLC (chloroform); however, there was a minor component at the origin.

Sulfonefluorescein dichloride was prepared as follows

In a 5 liter 3-necked round-bottom flask equipped with a paddle stirrer, a reflux condenser and a thermometer was placed 1.5 liters of ethyl acetate which was then cooled to 0° C. using an ice bath. Sulfonefluorescein (250 g) was added followed by 200 ml of thionyl chloride. The temperature rose slightly. The temperature was allowed to fall back to 0° C. 750 ml of N,N-dimethylformamide (DMF) was then added all at once. The temperature rose to about 30° C. After the additions were completed, the mixture was stirred for 1 hour. The ice bath was removed to allow the temperature of the reaction mixture to rise to room temperature after which the mixture was placed on a steam bath and heated to reflux with stirring. During heating the mixture became lighter in color and thicker. (The color was brown.) After refluxing 10 to 15 minutes the reaction mixture was placed in an ice bath and cooled to 0° C. with stirring continuing. The cold reaction mixture was filtered and washed with cooled 15% DMF/ethyl acetate solution until the color of the precipitate became as light as possible, then washed with ether. After sucking under a rubber dam, the sulfonefluorescein dichloride was air dried. Yield 184.3 g (68%); 99.7% pure by L. C.

Methanolic solutions of the compounds prepared in Examples 1 and 2 were added to a series of buffered solutions having a pH of 4, 5, 6 and 7, respectively, in order to determine the approximate pH at which these compounds become colored as the pH drops below alkaline values. As a comparison, the following compound disclosed in Beilstein's Handbuch der Organischen Chemie, Vol. 27, p. 544, also was added as a methanolic solution to a series of buffers.

As discussed previously, the subject light-screening compounds are pH-sensitive dyes that are in their colored form at about pH 4 or below and as evident from the results shown above, they are converted to their colorless form when contacted with aqueous base. In their colored form, the sulfamphthalein ring is open, for example,

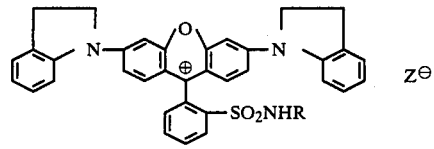

wherein R is hydrogen or alkyl and Z is an anion, and in their colorless form, the sulfamphthalein ring is closed

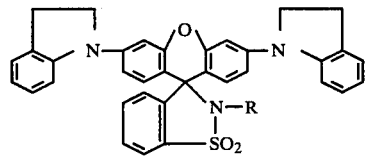

Because the subject compounds remain colorless at the pH's normally encountered during processing subsequent to being converted to their colorless form, they may be retained in a photographic film unit, e.g., a photosensitive element without the possibility of color reappearing in time. Typically, dyes may be selected for use as antihalation dyes, e.g., in a non-light-sensitive layer positioned intermediate a photosensitive silver halide emulsion layer and the support. Also, dyes may be selected for use as color correction filter dyes where absorption of light within a particular wavelength range during exposure is desirable for achieving appropriate color balance.

Whether used for antihalation, color correction or other photographic light-screening applications, the subject compounds, of course, should be in their colored or light-absorbing form initially, and thus, they should be incorporated in a layer having sufficient acidity to render the compounds colored. Useful layers include polymers which contain acid groups, e.g., carboxylic acid and sulfonic acid groups and polymeric acid or other polymeric layers containing polymeric or monomeric organic acids added in the amount necessary to give the level of acidity required for converting the selected dye compound to its colored form. The amount of additional acid needed, if any, may be readily determined empirically.

The use of the subject compounds as photographic light-screening dyes is disclosed and claimed in copending U.S. patent application Ser. No. 194,468 of Richard L. Cournoyer and James W. Foley filed concurrently herewith. For convenience, the specification of said application is specifically incorporated herein.

Since certain changes may be made in the hereinafter defined subject matter without departing from the scope of the invention herein involved, it is intended that all matter contained in the above description and examples be interpreted as illustrative and not in a limiting sense.

What is claimed is:

1. A compound of the formula

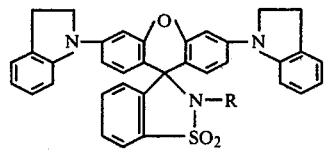

wherein R is hydrogen or alkyl.

2. The compound

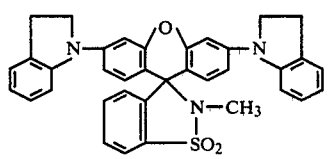

3. The compound

* * * * *